US008388537B2

(12) United States Patent
Umemura et al.

(10) Patent No.: US 8,388,537 B2
(45) Date of Patent: Mar. 5, 2013

(54) ULTRASONIC IMAGING APPARATUS

(75) Inventors: Shinichiro Umemura, Sendai (JP); Takashi Azuma, Sagamihara (JP)

(73) Assignee: Hitachi Medical Corporation, Tokyo (JP)

( * ) Notice: Subject to any disclaimer, the term of this patent is extended or adjusted under 35 U.S.C. 154(b) by 225 days.

(21) Appl. No.: 12/810,327

(22) PCT Filed: Aug. 28, 2008

(86) PCT No.: PCT/JP2008/065360
§ 371 (c)(1),
(2), (4) Date: Jun. 24, 2010

(87) PCT Pub. No.: WO2009/087792
PCT Pub. Date: Jul. 16, 2009

(65) Prior Publication Data
US 2010/0280376 A1    Nov. 4, 2010

(30) Foreign Application Priority Data
Jan. 10, 2008    (JP) .................................. 2008-002904

(51) Int. Cl.
*A61B 8/14*    (2006.01)
(52) U.S. Cl. ........ 600/443; 600/437; 600/449; 600/458; 600/459
(58) Field of Classification Search .................. 600/437, 600/443, 458, 459
See application file for complete search history.

(56) References Cited

U.S. PATENT DOCUMENTS

| 4,255,977 | A | * | 3/1981 | Newhouse et al. | ........ 73/861.25 |
| 6,095,980 | A | | 8/2000 | Burns et al. | |
| 6,458,084 | B2 | * | 10/2002 | Tsao et al. | ..................... 600/443 |
| 7,691,064 | B2 | * | 4/2010 | Cerofolini | ..................... 600/458 |
| 8,118,745 | B2 | * | 2/2012 | Umemura et al. | ............ 600/437 |
| 2003/0073903 | A1 | * | 4/2003 | Sato | ................................ 600/437 |
| 2004/0059221 | A1 | | 3/2004 | Azuma et al. | |
| 2005/0256404 | A1 | | 11/2005 | Sato | |
| 2009/0076392 | A1 | * | 3/2009 | Oshiki et al. | .................. 600/459 |
| 2010/0280376 | A1 | * | 11/2010 | Umemura et al. | ............ 600/443 |

FOREIGN PATENT DOCUMENTS

| JP | 11-137546 | 5/1999 |
| JP | 2003-102726 | 4/2003 |
| JP | 2004-113364 | 4/2004 |
| JP | 2005-319177 | 11/2005 |

* cited by examiner

*Primary Examiner* — Tse Chen
*Assistant Examiner* — Baisakhi Roy
(74) *Attorney, Agent, or Firm* — Antonelli, Terry, Stout & Kraus, LLP.

(57) ABSTRACT

An echo signal reflected from a microbubble contrast agent is discriminated from an echo signal generated upon reflection of a nonlinearly propagated transmission pulse from the body tissues without degradation of the axial resolution, by performing transmission/reception twice or less which would hardly decrease the imaging speed. By detecting a difference in phase of the second harmonic component based on the fundamental component included in the echo signal, an echo signal generated upon nonlinear reflection from a microbubble contrast agent is discriminated from an echo signal generated upon linear reflection of a nonlinearly propagated transmission pulse from the body tissues. The phase of the second harmonic component is detected through phase sensitive detection in which the square of the fundamental component is used as a reference wave. Concurrently, a pulse inversion method is used to extract the second harmonic component included in the original echo signal, whereby degradation of the axial resolution is prevented.

19 Claims, 9 Drawing Sheets

Tissue echo

(Stiff reflector)

(Soft reflector)

Contrast echo

Tissue echo

(Stiff reflector)

(Soft reflector)

Contrast echo

Tissue echo

Reception signal A

Reception signal B

Contrast echo

Reception signal A

Reception signal B

Tissue echo

Summed signal

Subtracted signal

Contrast echo

Summed signal

Subtracted signal

Reference wave for tissue echo

Reference wave for contrast echo

Tissue echo

Phase sensitive detector
Input signal (Summed signal
and reference signal)

Phase sensitive detector
Output signal

Contrast echo

Phase sensitive detector
Input signal (Summed signal
and reference signal)

Phase sensitive detector
Output signal

ULTRASONIC IMAGING APPARATUS

TECHNICAL FIELD

The present invention relates to an apparatus that captures an echo image of a object using ultrasound, and in particular, to an ultrasonic imaging apparatus having a mode that combines the use of microbubble contrast agents.

BACKGROUND ART

Ultrasonic imaging apparatuses used for medical imaging diagnoses are capable of observing, using an ultrasonic pulse echo method, a tomographic image of soft tissue of a living body, an image of blood flowing through a living body, or the like by displaying the image on a monitor substantially in real time. Further, nowadays, contrast-enhanced ultrasonography has been developed in which an ultrasonic contrast agent that contains stabilized microbubbles as the main component is administered through intravenous injection or the like, so that an image of the blood circulatory system or an organ such as a liver, which can easily be perfused with the contrast agent, is emphatically extracted.

Further, a microbubble has a characteristic that it functions as a nonlinear reflector, that is, it generates a readily detectable nonlinear echo even at a transmission ultrasound pressure in the range that ultrasonic diagnosis can be safely conducted. Such a characteristic can be utilized to discriminate an echo from the contrast agent from echoes from the surrounding body tissue. In the early days when the development of the contrast-enhanced ultrasonography using microbubbles was just started, a method was used in which the fundamental component included in a nonlinear echo signal was suppressed with the use of a bandpass filter to extract the second harmonic component. However, there has been a problem in that the use of the bandpass filter could increase the length of the echo signal in the time direction, and thereby degrading the axial resolution of the resulting ultrasonic echo image. Such a problem was solved with the pulse inversion method (Patent Document 1). Specifically, this method involves two times of transmission/reception with two transmission pulses whose polarities are reversed with respect to each other, and summing the obtained reception echo signals, so that the second harmonic component is extracted while the fundamental component is suppressed independently of a bandpass filter. Although this method would require twice the imaging time, it has a characteristic feature that it can extract nonlinear signal components without degradation of the axial resolution. Thus, a variety of methods have been developed based on such a method and have been put into practical use.

There has also been proposed a method for detecting inversion or non-inversion of a reception pulse in diagnostic ultrasonic imaging (Patent Document 2). In this method, the phase of the second harmonic echo component is detected through phase sensitive detection (PSD) in which the square of the fundamental echo component is used as a reference wave.
Patent Document 1: U.S. Pat. No. 6,095,980 B1
Patent Document 2: JP 2004-113364 A

DISCLOSURE OF THE INVENTION

Problems to be Solved by the Invention

As the development of the contrast-enhanced ultrasonography using nonlinear echo components has advanced, it has been clarified that the signal level of a nonlinear echo that is generated upon reflection of nonlinear components, which are generated when a transmission pulse wave propagates through the body tissue, from a linear reflector such as the body tissues cannot be ignored with respect to the signal level of a nonlinear echo returned from a nonlinear reflector such as a contrast agent. In order to solve such a problem, a variety of methods have been proposed in which transmission/reception are performed three times or more. However, there still remains another problem to be solved that the imaging speed could further decrease.

The present invention has been made in view of both the characteristic features and problems of the conventional techniques described above. It is an object of the present invention to overcome the characteristic features and problems of the conventional techniques and provide an ultrasonic imaging apparatus that discriminates an echo signal reflected from a microbubble contrast agent from an echo signal generated when a nonlinearly propagated transmission pulse is reflected from the body tissues without degradation of the axial resolution, by performing transmission/reception twice or less which would hardly decrease the imaging speed.

Means for Solving the Problems

A phase relationship, which is based on the fundamental component, of the second harmonic component included in an echo signal reflected from a microbubble differs from a phase relationship, which is based on the fundamental component, of the second harmonic component included in an echo signal generated upon reflection of a transmission pulse wave, which has propagated nonlinearly through the body tissue, from a linear reflector such as the body tissues. Thus, such phase relationships can potentially be discriminated from each other using a phase sensitive detection method.

FIG. 1 is a diagram showing, for each of echo signals (the upper and middle diagrams) generated upon linear reflection of a nonlinearly propagated transmission pulse from the body tissues and an echo signal (the lower diagram) generated upon nonlinear reflection from a microbubble contrast agent, a comparison result between the phase of the second harmonic component (solid line) and the phase of the fundamental component (dotted line; shown with the shrunk amplitude). When an echo signal (the upper diagram) generated upon linear reflection of a nonlinearly propagated transmission pulse from a "stiff" reflector whose acoustic impedance increases in the depth direction is seen, the waves of the fundamental component and the second harmonic component are substantially in phase when both the waves rise from the negative level to the positive level. When an echo signal (the middle diagram) generated upon linear reflection of a nonlinearly propagated transmission pulse from a "soft" reflector whose acoustic impedance decreases in the depth direction is seen, the waves of the fundamental component and the second harmonic component are substantially in phase when both the waves fall from the positive level to the negative level as the phase is reversed by the reflection. Meanwhile, when an echo signal (the lower diagram) generated upon nonlinear reflection from a microbubble contrast agent is seen, the waves of the fundamental component and the second harmonic component are substantially in phase when both the waves reach the positive peaks. According to the present invention, such a difference in phase of the second harmonic component based on the fundamental component is detected, whereby an echo signal generated upon nonlinear reflection from a microbubble contrast agent is discriminated from an echo signal generated upon linear reflection of a nonlinearly propagated transmission pulse from the body tissues.

FIG. 2 shows the second harmonic component (dotted line) extracted from a signal obtained by squaring or full-wave rectifying the fundamental component shown in FIG. 1, which is overlaid on the second harmonic component (solid line) of the original signal. As was expected from FIG. 1, when the echo signal (the lower diagram) generated upon nonlinear reflection from a microbubble contrast agent is seen, the waves of both the second harmonic components indicated by the solid line and dotted line are substantially in phase. However, when the echo signals (the upper and middle diagrams) generated upon linear reflection of a nonlinearly propagated transmission pulse from the body tissues are seen, the waves are substantially 90° out of phase with respect to each other in both cases of the "stiff" reflector (the upper diagram) and the "soft" reflector (the middle diagram). Thus, by performing phase sensitive detection (PSD) in which the phase change (shift) between the two waves is detected, it is possible to discriminate an echo signal generated upon nonlinear reflection from a microbubble contrast agent from an echo signal generated upon linear reflection of a nonlinearly propagated transmission pulse from the body tissues.

Advantages of the Invention

According to the present invention, it is possible to detect and distinguish an echo signal generated upon nonlinear reflection from a microbubble contrast agent from an echo signal generated upon linear reflection of a nonlinearly propagated transmission pulse from the body tissues without degradation of the axial resolution, by performing transmission/reception twice or less which would hardly decrease the imaging speed, and display such a signal as an echo image for ultrasonic diagnosis.

DESCRIPTION OF SYMBOLS

Figure 1:
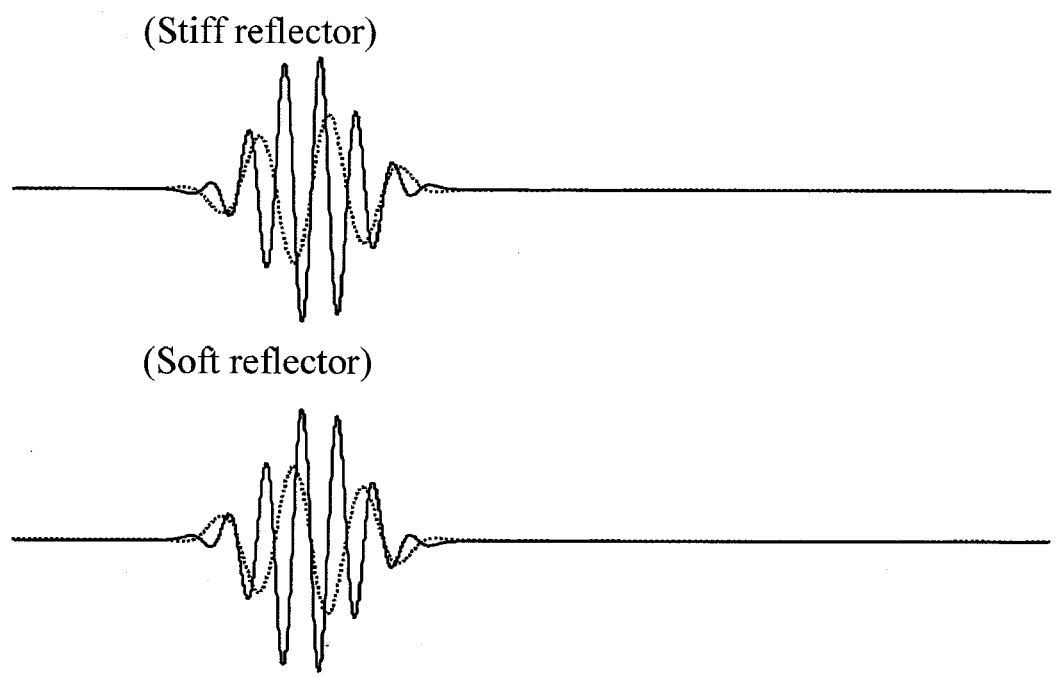
FIG. 1 is a diagram showing, for each of echo signals generated upon linear reflection of a nonlinearly propagated transmission pulse from the body tissues and an echo signal generated upon nonlinear reflection from a microbubble contrast agent, a comparison result between the phase of the second harmonic component (solid line) and the phase of the fundamental component (dotted line; shown with the shrunk amplitude).
Figure 1:
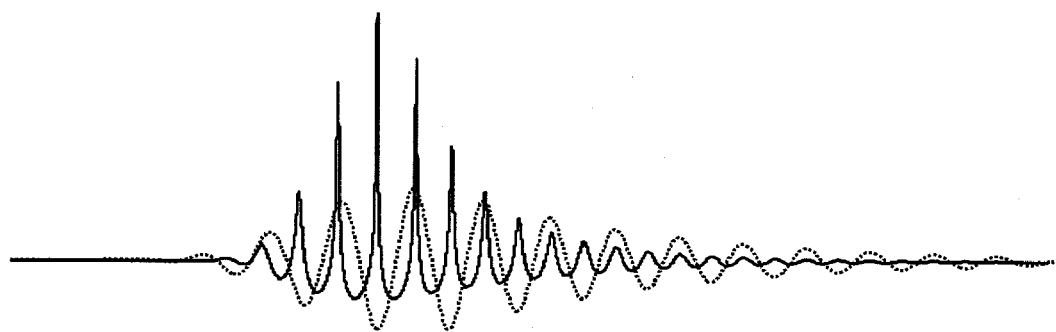
Figure 2:
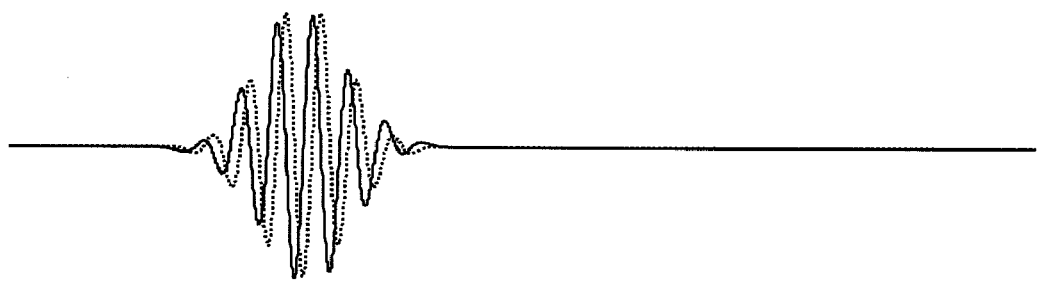
FIG. 2 is a diagram showing the second harmonic component (dotted line) extracted from a signal obtained by squaring or full-wave rectifying the fundamental component shown in FIG. 1, which is overlaid on the second harmonic component (solid line) of the original signal.
Figure 2:
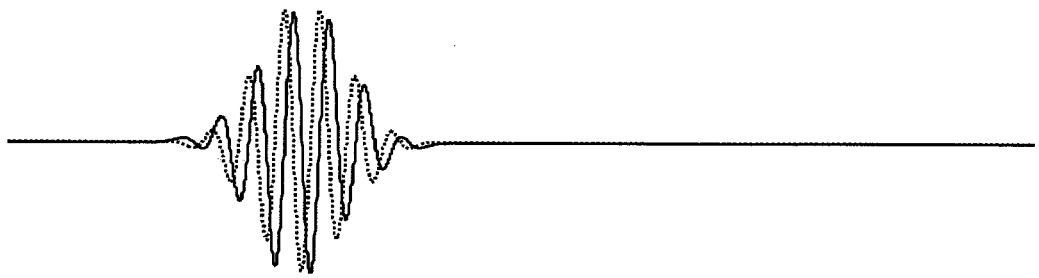
Figure 2:
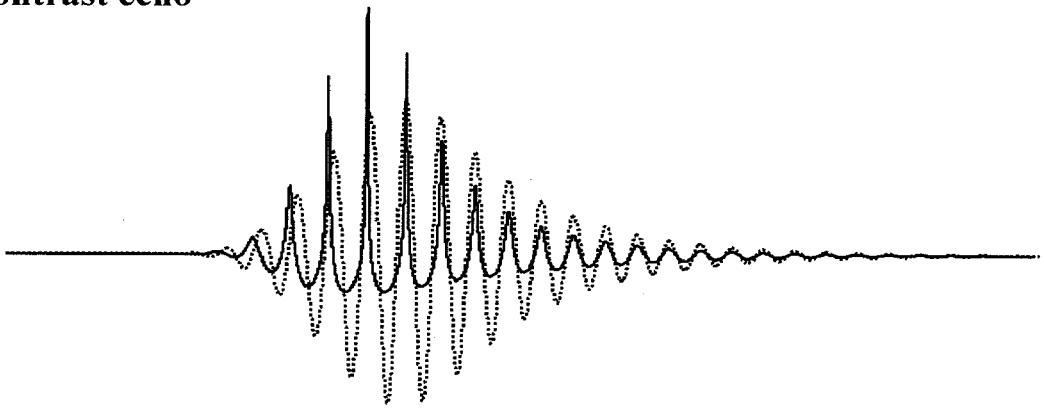

1 ultrasonic probe
2 transmission/reception switches
3 transmission beamformer
5 phase correction processor
7 scan converter
8 display
9 sequence controller
10 reception beamformer
21 reception data memory A
22 reception data memory B
30 summed signal processor
31 filter
40 squared signal processor
41 filter
60 phase sensitive detector
61 low pass filter

BEST MODES FOR CARRYING OUT THE INVENTION

Hereinafter, embodiments of the present invention will be described in detail with reference to the accompanying drawings.

Figure 3:
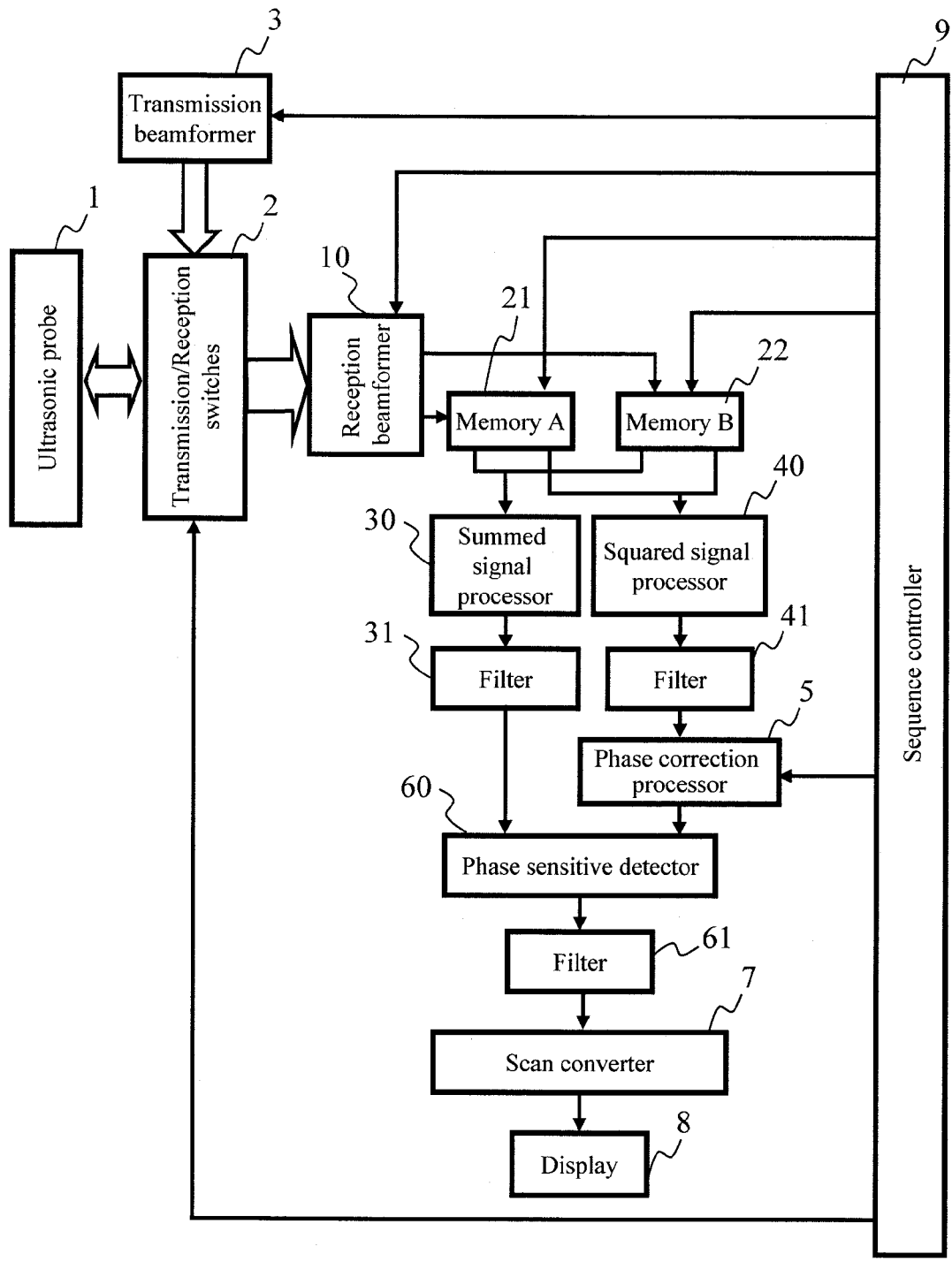
FIG. 3 is a diagram showing a configuration example of an ultrasonic imaging apparatus in accordance with the present invention.

FIG. 3 is a diagram showing a configuration example of an ultrasonic imaging apparatus in accordance with the present invention. This apparatus is capable of discriminating an echo signal generated upon nonlinear reflection from a microbubble contrast agent from an echo signal generated upon linear reflection of a nonlinearly propagated transmission pulse from the body tissues, and displaying such an echo signal.

An ultrasonic probe 1 transmits an ultrasonic pulse to a object (not shown), and receives an ultrasonic echo from the object. A transmission beamformer 3, under the control of a sequence controller 9, imparts directivity to a transmission pulse. In addition, two kinds of transmission waveforms are selectively used. The transmission pulse is transmitted to the ultrasonic probe 1 via transmission/reception SWs (switches) 2 that are also under the control of the sequence controller 9, and is transmitted as ultrasound. An ultrasound echo, which has returned to the ultrasonic probe 1 after being reflected from or scattered within the object, is converted into an electric signal with the ultrasonic probe 1, and is then transmitted to a reception beamformer 10 via the transmission/reception switches 2 again. The reception beamformer 10, under the control of the sequence controller 9, performs dynamic focus for adjusting the delay time in accordance with the wave reception timing based on the wave transmission timing.

Figure 4:
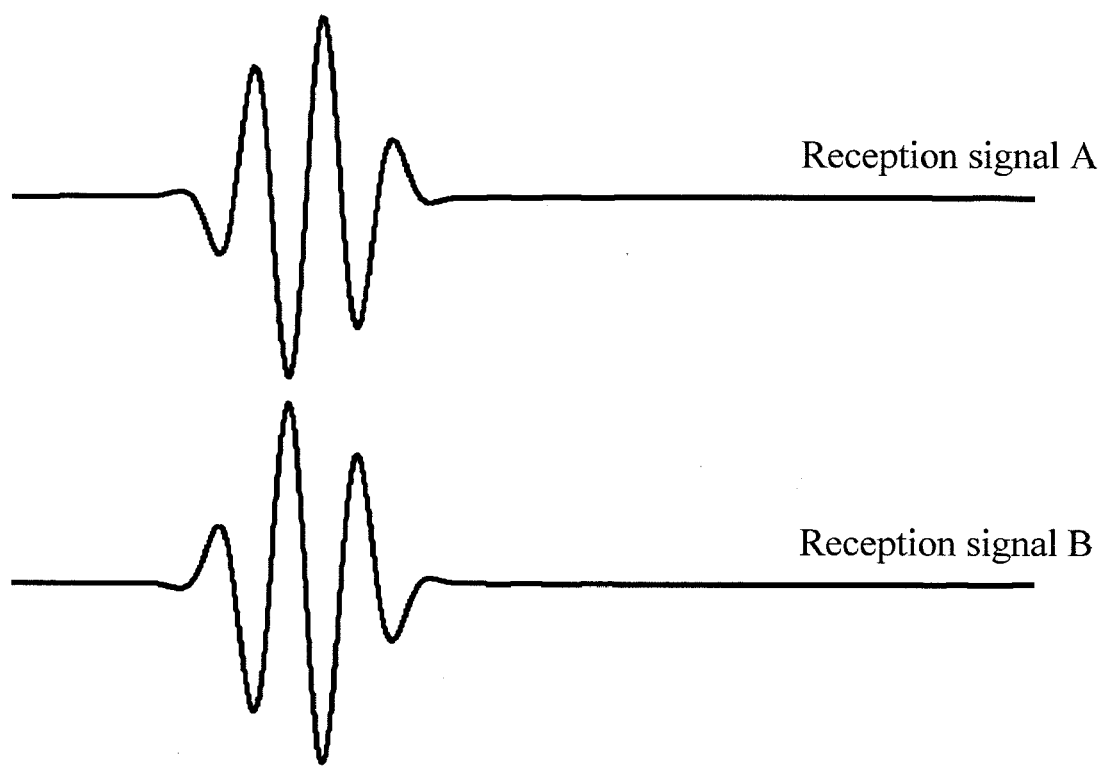
FIG. 4 is a diagram showing the waveforms of echo signals generated upon linear reflection from the body tissues and the waveforms of echo signals generated upon nonlinear reflection from a microbubble contrast agent.
Figure 4:
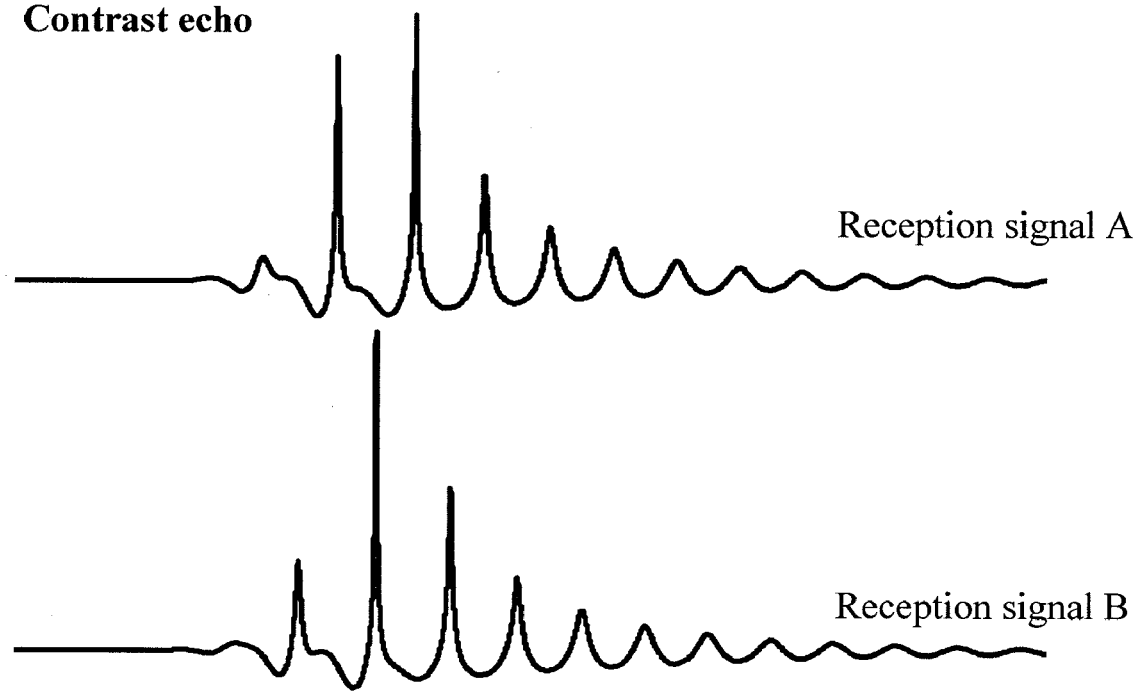

In this embodiment, a first transmission waveform such as a pulse signal shown in the upper diagram of FIG. 4 and a second transmission waveform such as a pulse signal (the second diagram from the above) obtained by reversing the polarity of the first transmission waveform are selectively used. A reception signal A obtained by transmitting the first transmission waveform is once stored in memory A 21, and a reception signal B obtained by transmitting the second transmission waveform is once stored in memory B 22. The two upper waveforms shown in FIG. 4 are echo signal waveforms generated upon linear reflection from the body tissues (in the case of a "stiff" reflector), and the two lower waveforms are echo signal waveforms generated upon nonlinear reflection from a microbubble contrast agent.

Figure 5:
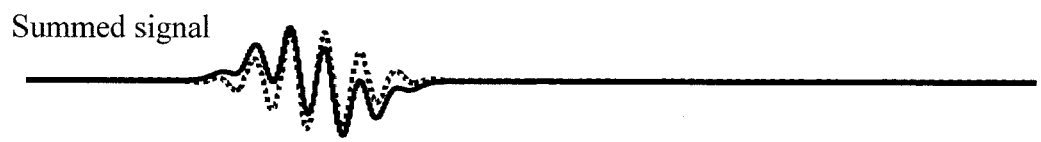
FIG. 5 is a diagram showing, for each of echo signals generated upon linear reflection from the body tissues and echo signals generated upon nonlinear reflection from a microbubble contrast agent, a summed signal waveform and a subtracted signal waveform.
Figure 5:
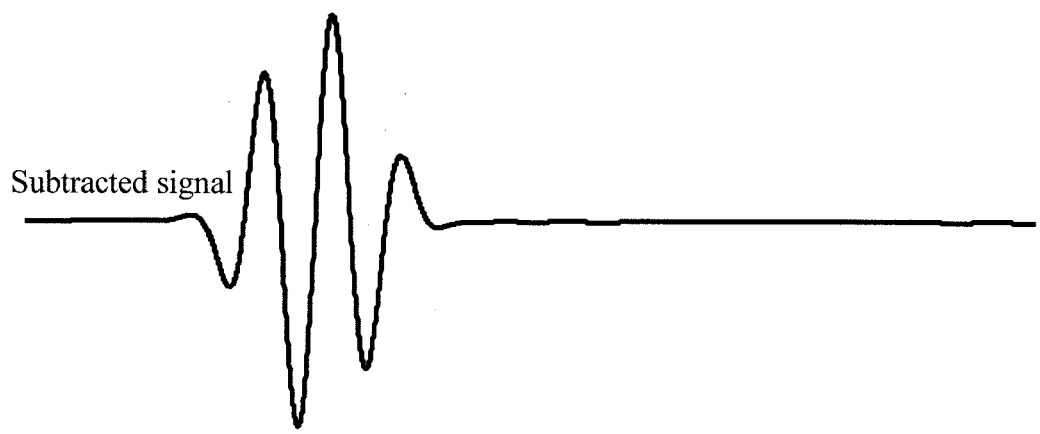
Figure 5:
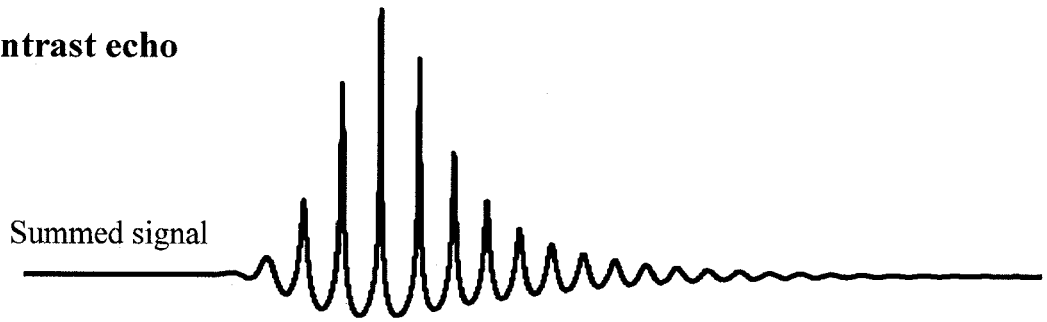
Figure 5:
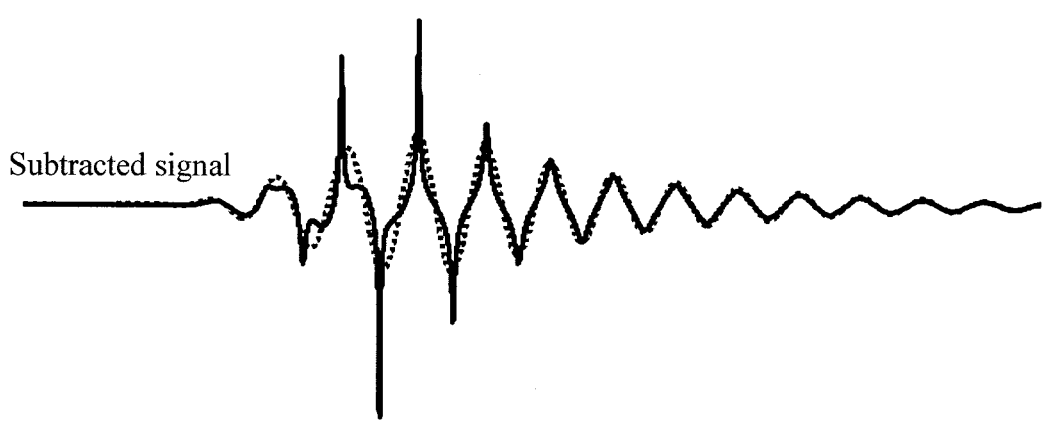

A summed signal processor 30 computes a summed signal of the reception signals A and B. The two upper waveforms shown in FIG. 5 are a summed signal waveform (the first diagram) and a subtracted signal waveform (the second diagram) of the echo signals generated upon linear reflection from the body tissues. In the first diagram, the dotted line indicates a signal obtained by passing the summed signal through a filter 31 to remove the low-frequency components. Meanwhile, the two lower waveforms shown FIG. 5 are a summed signal waveform (the third diagram) and a subtracted signal waveform (the fourth diagram) of the echo signals generated upon nonlinear reflection from a microbubble contrast agent. Upon computation of the summed signal, the fundamental component of the ultrasound is removed. Accordingly, it is possible, as long as nonlinear components generated due to the propagation through a living body can be discriminated from a contrast signal, to achieve the object of the invention of discriminating between an echo signal from a living body and an echo signal from a contrast agent. Described hereinafter is a specific method for discriminating between nonlinear components generated due to the propagation through a living body and a contrast signal.

Figure 6:
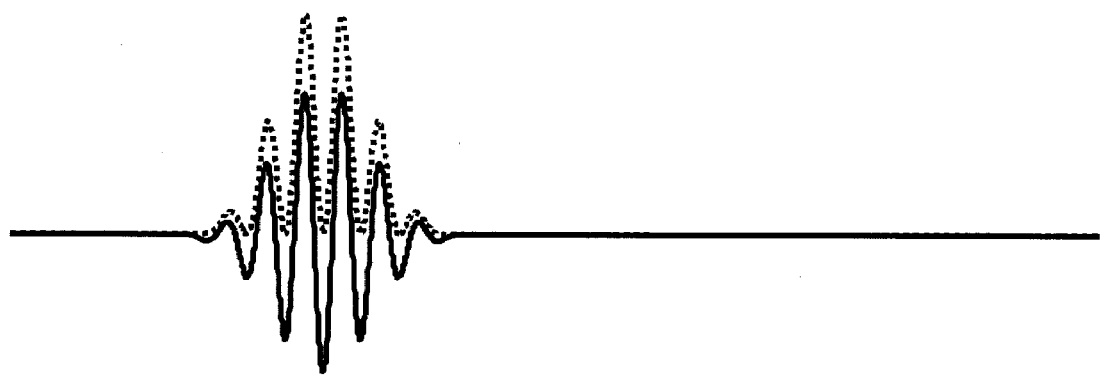
FIG. 6 is a diagram showing, for each of echo signals generated upon linear reflection from the body tissues and echo signals generated upon nonlinear reflection from a microbubble contrast agent, the waveforms of reference signals used for phase sensitive detection.
Figure 6:
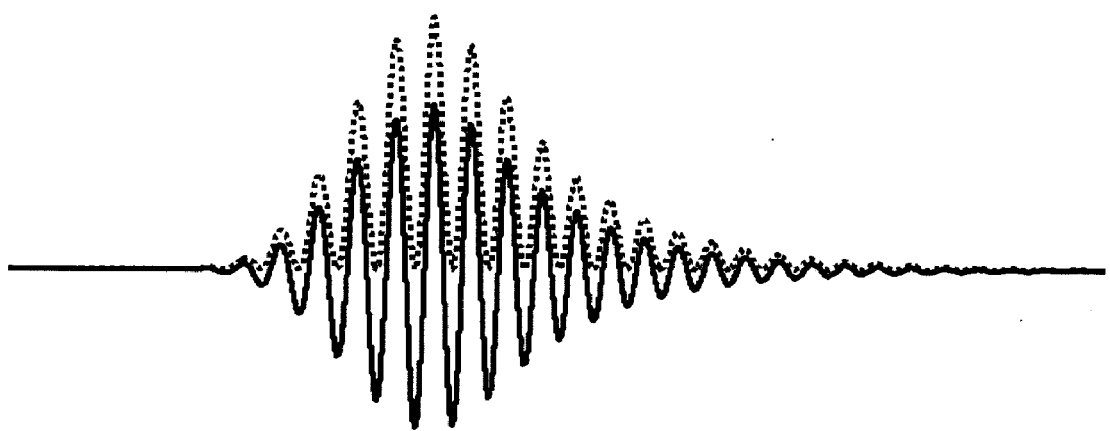

In a squared signal processor 40 and a filter 41, the aforementioned subtracted signal or one of the reception signals A and B is squared or full-wave rectified (or the absolute value is determined) to generate a signal to be used as a reference signal for phase sensitive detection (PSD). FIG. 6 shows the phase-sensitive-detection reference signals for an echo signal (the upper diagram) generated upon linear reflection from the body tissues and an echo signal (the lower diagram) generated upon nonlinear reflection from a microbubble contrast agent. In the drawings, the dotted line indicates a squared signal, and the solid line indicates a reference signal obtained by passing the squared signal through the filter 41 to remove the low-frequency components.

A phase sensitive detector 60 performs phase sensitive detection (PSD) between the summed signal and the reference signal. Phase sensitive detection is the process of multiplying the reference signal by the input signal and passing the resulting signal through a low pass filter; it is the process of extracting signals with the same frequency and the same phase. Specifically, the phase sensitive detector 60 performs the following process.

Figure 7:
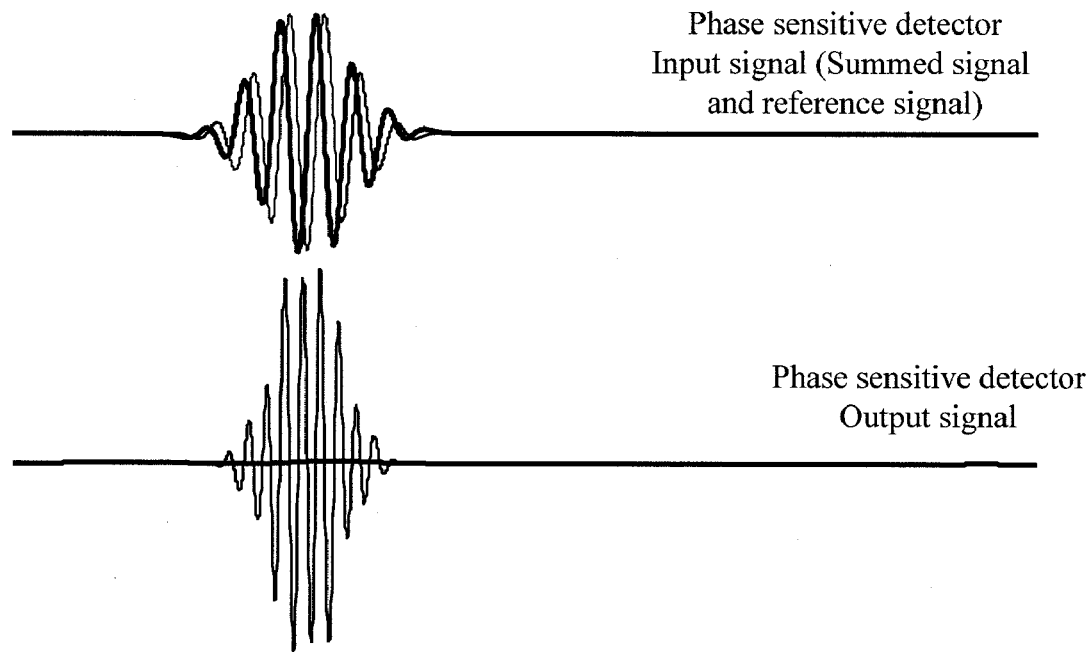
FIG. 7 is a diagram showing, for each of echo signals generated upon linear reflection from the body tissues and echo signals generated upon nonlinear reflection from a microbubble contrast agent, input signal waveforms and output signal waveforms of a phase sensitive detector.
Figure 7:
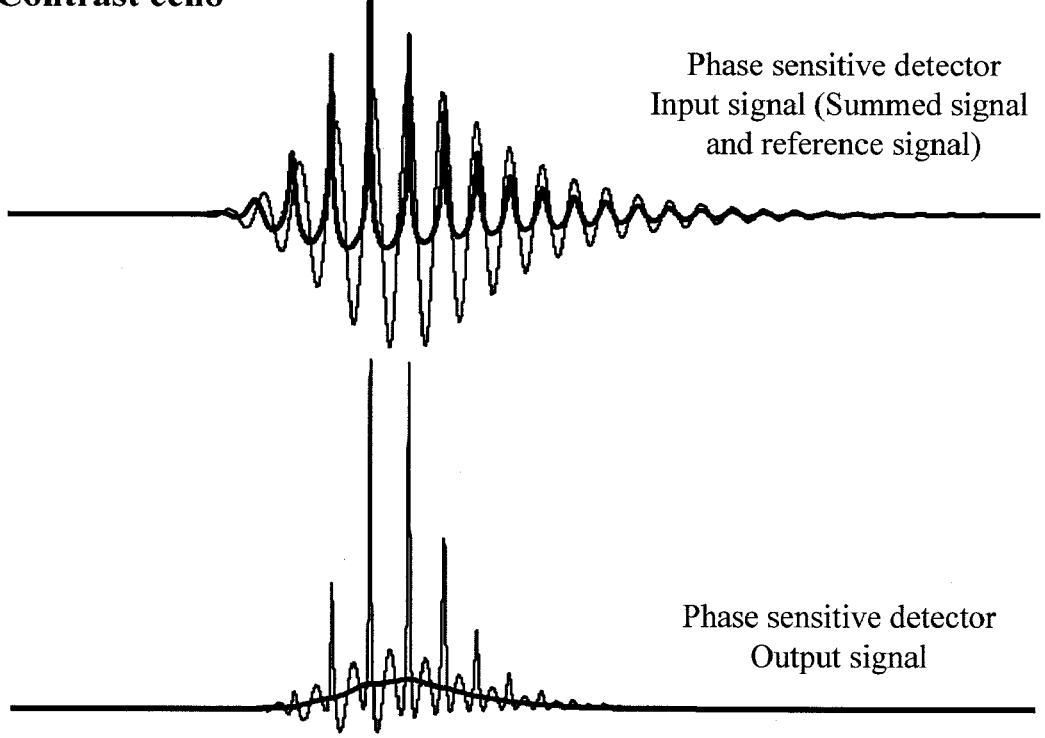

FIG. 7 shows, for each of echo signals (the first and second diagrams) generated upon linear reflection from the body tissues and echo signals (the third and fourth diagrams) generated upon nonlinear reflection from a microbubble contrast agent, an input signal (each upper diagram) and an output signal (each lower diagram) of the phase sensitive detector 60. In the first and third diagrams, a waveform indicated by the solid line is the summed signal and a waveform indicated by the thin line is the reference signal. In the second and fourth diagrams, a waveform indicated by the thin line is the output signal, and a waveform indicated by the solid line is a signal obtained by passing the output signal through a low pass filter 61 to remove the high-frequency components. Such signals are input to a scan converter 7 and then are displayed as images on a display 8. As indicated by the solid line in the second and fourth diagrams, through the phase sensitive detection (PSD), the echo signal (the fourth diagram) generated upon nonlinear reflection from the microbubble contrast agent is detected while the echo signal (the second diagram) generated upon linear reflection from the body tissues is suppressed.

Figure 8:
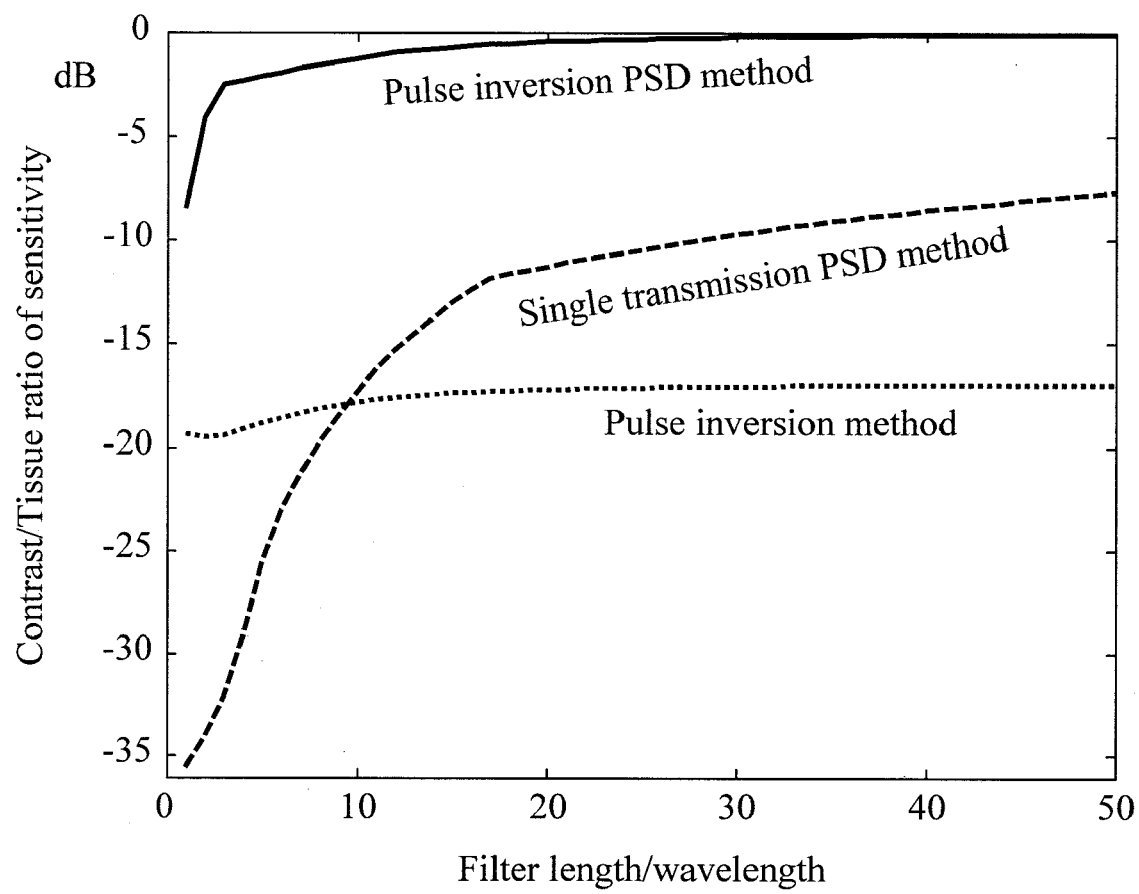
FIG. 8 is a diagram showing the relative value of the (contrast/tissue) ratio of sensitivity as the function of the length of a low pass filter in the time-axis direction.
Figure 9:
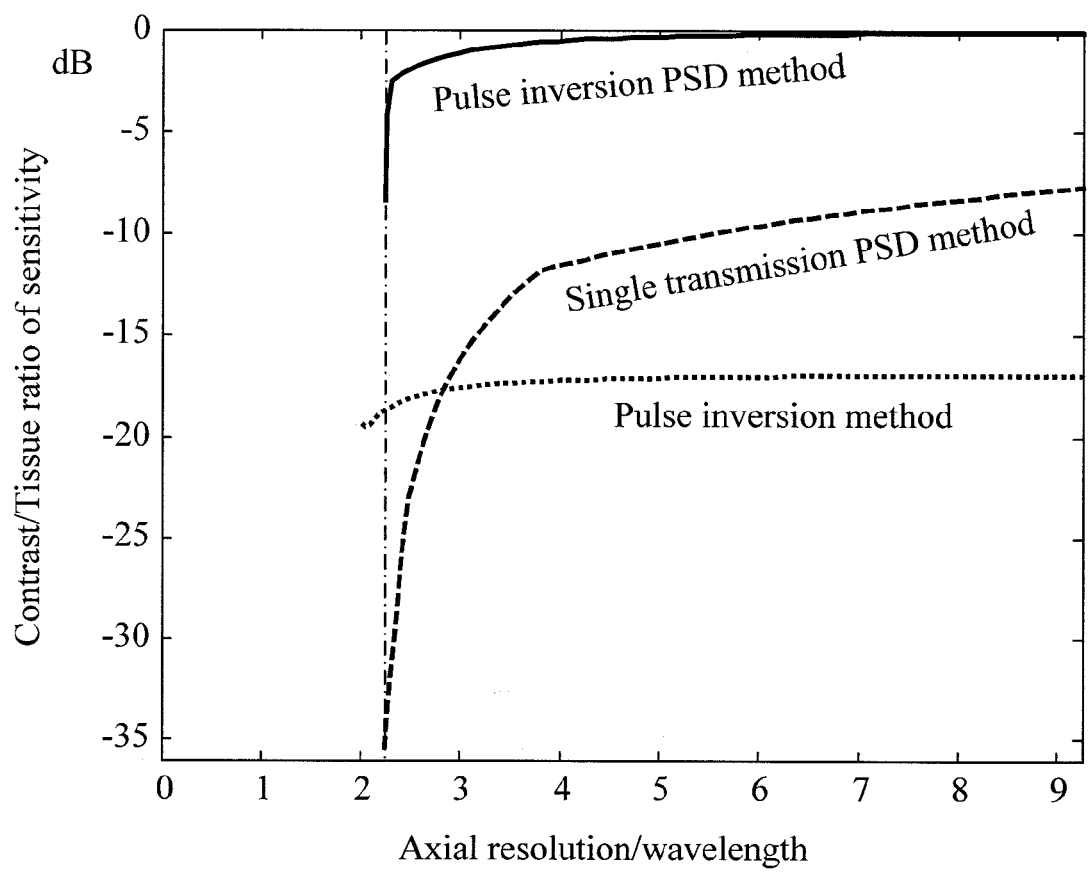
FIG. 9 is a diagram showing the relative value of the (contrast/tissue) ratio of sensitivity as the function of the realized axial resolution.

FIG. 8 is a plot diagram showing a comparison result between the relative value of the ratio of sensitivity, namely, the (contrast/tissue) ratio of sensitivity when the length of the low pass filter 61 in the time-axis direction is changed and those of the other methods. With the pulse inversion PSD method of the present invention, a satisfactory sensitivity ratio, which is higher than the sensitivity ratios of the other methods by about 10 dB or more, can be obtained by using a filter length of several wavelengths or more. In contrast, when a pulse inversion method is used alone, an increase in the sensitivity ratio by the use of a low pass filter is hardly seen, and the sensitivity is lower than that of the pulse inversion PSD method of the present invention by 15 dB or more. Meanwhile, when a PSD method is performed using a signal obtained through a single transmission, a filter length of ten wavelengths or more is required in order to obtain a satisfactory sensitivity ratio. In this case, however, the sensitivity is still lower than that of the pulse inversion PSD method of the present invention by about 10 dB. FIG. 9 is a plot diagram of the axial resolution that can obtain the result of FIG. 8. FIG. 9 can confirm that the pulse inversion PSD method of the present invention can realize a significantly higher (contrast/tissue) ratio of sensitivity than those of the other methods without hardly degrading the axial resolution.

The phase correction processor 5 corrects the phase rotation of an echo signal generated by the ultrasonic probe 1, the transmission/reception switches 2, the transmission beamformer 3, the reception beamformer 10, and the propagation of ultrasound through the living body as the function of the time elapsed since the transmission such that the phase sensitive detector will perform a desired operation. Such correction can be calculated from the characteristics of the circuit elements that constitute the apparatus or can be performed based on the calibration data acquired before factory shipment. It should be noted that the phase sensitive detector can be provided on the side of the summed signal. Alternatively, two phase sensitive detectors can be provided and the phase correction processor can be provided following the phase sensitive detector.

The invention claimed is:

1. An ultrasonic imaging apparatus comprising:
   an ultrasonic probe that transmits and receives an ultrasonic signal to/from a object;
   a transmission controller that controls transmission of, for ultrasonic signals transmitted by the ultrasonic probe, a first transmission ultrasonic signal and a second transmission ultrasonic signal obtained by reversing the polarity of the first transmission ultrasonic signal;
   a signal processor that detects and processes to obtain, for ultrasonic signals received by the ultrasonic probe, a phase shift of a summed signal of a first reception signal and a second reception signal, the first reception signal being based on the first transmission ultrasonic signal and the second reception signal being based on the second transmission ultrasonic signal; and
   a signal discriminator that discriminates between a reflection echo signal from a contrast agent and a reflection echo signal from body tissue of the object, based on the phase shift of the summed signal that has been detected and processed with the signal processor.

2. The ultrasonic imaging apparatus according to claim 1, wherein the signal processor detects the phase shift using a reference wave that is obtained based on a difference signal between the first reception signal and the second reception signal or one of the first and second reception signals.

3. The ultrasonic imaging apparatus according to claim 1, wherein the signal processor detects the phase shift using a reference wave, the reference wave being obtained based on a signal that is obtained by squaring or full-wave rectifying a difference signal between the first reception signal and the second reception signal or one of the first and second reception signals.

4. The ultrasonic imaging apparatus according to claim 1, wherein the phase shift is detected using, as a reference wave, a second harmonic component included in the signal obtained by the squaring or full-wave rectifying.

5. The ultrasonic imaging apparatus according to claim 1, wherein the signal processor detects the phase shift using a reference wave that is obtained based on an absolute value of a difference signal between the first reception signal and the second reception signal or an absolute value of one of the first and second reception signals.

6. The ultrasonic imaging apparatus according to claim 1, wherein the signal processor performs phase sensitive detection as the detection of the phase shift.

7. The ultrasonic imaging apparatus according to claim 1, further comprising a phase correction processor that performs phase correction to the signal, the phase shift of which is detected.

8. The ultrasonic imaging apparatus according to claim 1, wherein the signal processor detects the phase shift by multiplying the reference wave by the difference signal between the first reception signal and the second reception signal or one of the first and second reception signals, and filtering a result of the multiplication.

9. The ultrasonic imaging apparatus according to claim 8, wherein the signal processor performs the filtering with a low pass filter.

10. The ultrasonic imaging apparatus according to claim 1, wherein the signal processor extracts signals with identical frequency and identical phase.

11. An ultrasonic imaging apparatus comprising:
an ultrasonic probe that transmits and receives an ultrasonic signal to/from a object;
a transmission controller that controls transmission of, for ultrasonic signals transmitted by the ultrasonic probe, a first transmission ultrasonic signal and a second transmission ultrasonic signal obtained by reversing the polarity of the first transmission ultrasonic signal;
a signal processor that detects and processes to obtain, for ultrasonic signals received by the ultrasonic probe, a phase shift of a summed signal of a first reception signal and a second reception signal, the first reception signal being based on the first transmission ultrasonic signal and the second reception signal being based on the second transmission ultrasonic signal; and
a signal discriminator that discriminates between a reflection echo signal from a contrast agent and a reflection echo signal from body tissue of the object, based on the phase shift of the summed signal that has been detected and processed with the signal processor, where the signal discriminator is configured to extract signals with a same frequency and a same phase, to discriminate between the reflection echo signal from the contrast agent and the reflection echo signal from body tissue of the object.

12. The ultrasonic imaging apparatus according to claim 11, wherein the signal processor detects the phase shift using a reference wave that is obtained based on a difference signal between the first reception signal and the second reception signal or one of the first and second reception signals.

13. The ultrasonic imaging apparatus according to claim 11, wherein the signal processor detects the phase shift using a reference wave, the reference wave being obtained based on a signal that is obtained by squaring or full-wave rectifying a difference signal between the first reception signal and the second reception signal or one of the first and second reception signals.

14. The ultrasonic imaging apparatus according to claim 11, wherein the phase shift is detected using, as a reference wave, a second harmonic component included in the signal obtained by the squaring or full-wave rectifying.

15. The ultrasonic imaging apparatus according to claim 11, wherein the signal processor detects the phase shift using a reference wave that is obtained based on an absolute value of a difference signal between the first reception signal and the second reception signal or an absolute value of one of the first and second reception signals.

16. The ultrasonic imaging apparatus according to claim 11, wherein the signal processor performs phase sensitive detection as the detection of the phase shift.

17. The ultrasonic imaging apparatus according to claim 11, further comprising a phase correction processor that performs phase correction to the signal, the phase shift of which is detected.

18. The ultrasonic imaging apparatus according to claim 11, wherein the signal processor detects the phase shift by multiplying the reference wave by the difference signal between the first reception signal and the second reception signal or one of the first and second reception signals, and filtering a result of the multiplication.

19. The ultrasonic imaging apparatus according to claim 18, wherein the signal processor performs the filtering with a low pass filter.

* * * * *